US00PP35742P2

(12) United States Plant Patent
Spil

(10) Patent No.: US PP35,742 P2
(45) Date of Patent: Apr. 9, 2024

(54) ***ECHINACEA* PLANT NAMED 'IFECSSCITR'**

(50) Latin Name: *Echinacea hybrida*
Varietal Denomination: IFECSSCITR

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/114,795

(22) Filed: Feb. 27, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS

PP28,827 P3 * 12/2017 van den Haak ..... A01H 5/02 Plt./428

OTHER PUBLICATIONS

CPVORegister S2/S3 version 4.9.9, retrieved on Jun. 14, 2023 at https://online.plantvarieties.eu/publicSearch?denomination=ifecsscitr, 2 pp. (Year: 2023).*
Ditoplant Export BV retrieved from the Internet at https://www.ditoplant.nl/?p=pagina&s=30&lang=en, pp. 1,8 (Year: 2023).*
Floraxchange retrieved from the Internet at https://www.floraxchange.nl/Artikel/Info/1175099/Echinacea-Sunseekers-Citrus, one page. (Year: 2023).*

* cited by examiner

*Primary Examiner* — June Hwu
(74) *Attorney, Agent, or Firm* — C. Anne Whealy

(57) ABSTRACT

A new and distinct cultivar of *Echinacea* plant named 'IFECSSCITR', characterized by its relatively compact and upright plant habit; moderately vigorous growth habit; freely branching habit; strong flowering stems; numerous single-type inflorescences with vivid yellow-colored ray florets and receptacle spines; and good garden performance.

2 Drawing Sheets

Figure 1:
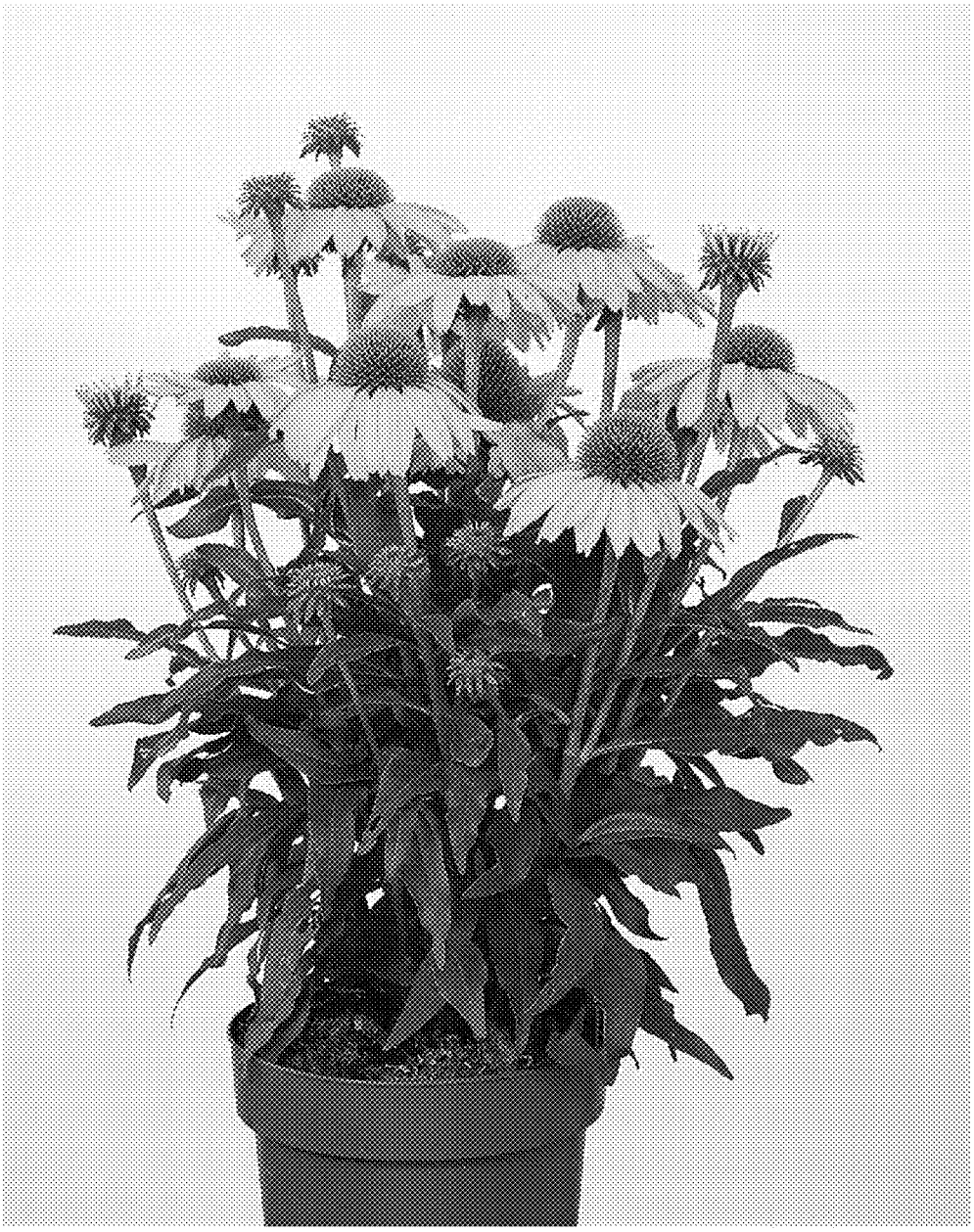

Botanical designation: *Echinacea hybrida.*
Cultivar denomination: 'IFECSSCITR'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 24, 2022, application number 2022/2655. Foreign priority is not claimed to this application.

BACKGROUND OF THE INVENTION

The present invention relates to a new and distinct cultivar of *Echinacea* plant, botanically known as *Echinacea hybrida*, and hereinafter referred to by the name 'IFECSSCITR'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from a cross-pollination by the Inventor in July, 2018 in Heerhugowaard, The Netherlands of a proprietary selection of *Echinacea hybrida* identified as code number 009-17-K062-01, not patented, as the female, or seed, parent with a proprietary selection of *Echinacea hybrida* identified as code number 009-17-K062-01, not patented, as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in August, 2019.

Asexual reproduction of the new *Echinacea* plant by in vitro meristem culture in a controlled environment in Heerhugowaard, The Netherlands since September, 2019 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSCITR'. These characteristics in combination distinguish 'IFECSSCITR' as a new and distinct *Echinacea* plant:

1. Relatively compact and upright plant habit.
2. Moderately vigorous growth habit.
3. Freely branching habit.
4. Strong flowering stems.
5. Numerous single-type inflorescences with vivid yellow-colored ray florets and receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are taller than plants of the female parent selection.
2. Plants of the new *Echinacea* have stronger and healthier foliage than plants the female parent selection.

Plants of the new *Echinacea* can be compared to plants of the male parent selection. Plants of the new *Echinacea* differ primarily from plants of the male parent selection in the following characteristics:

1. Plants of the new *Echinacea* are more compact than plants of the male parent selection.
2. Inflorescences of plants of the new *Echinacea* have a single whorl of ray florets whereas inflorescences of plants of the male parent selection have two whorls of ray florets.
3. Ray florets of plants of the new *Echinacea* are darker yellow in color than ray florets of plants of the male parent selection.

Plants of the new *Echinacea* can be compared to plants of *Echinacea purpurea* 'Apecssiye', disclosed in U.S. Plant Pat. No. 28,827. In side-by-side comparisons, plants of the new *Echinacea* differ primarily from plants of 'Apecssiye' in the following characteristics:

1. Plants of the new *Echinacea* are more compact than plants of 'Apecssiye'.
2. Plants of the new *Echinacea* are more freely flowering than plants of 'Apecssiye'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSCITR' grown in a container.

Figure 2:
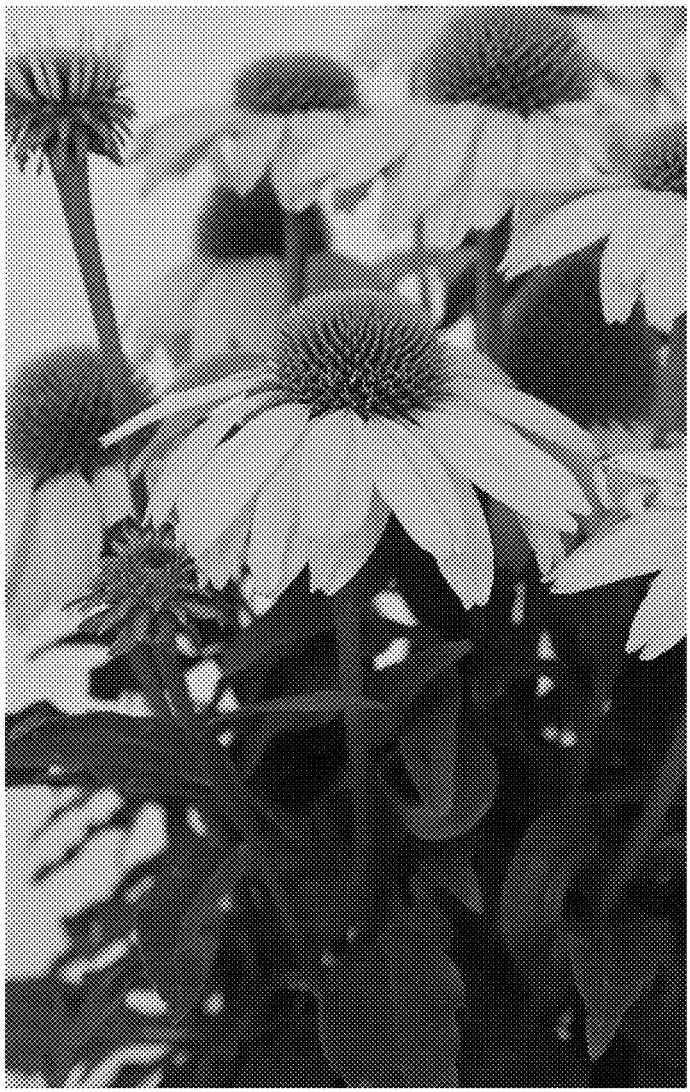

The photograph at the top of the second sheet (FIG. 2) is a close-up view of typical inflorescences of 'IFECSSCITR'.

Figure 3:
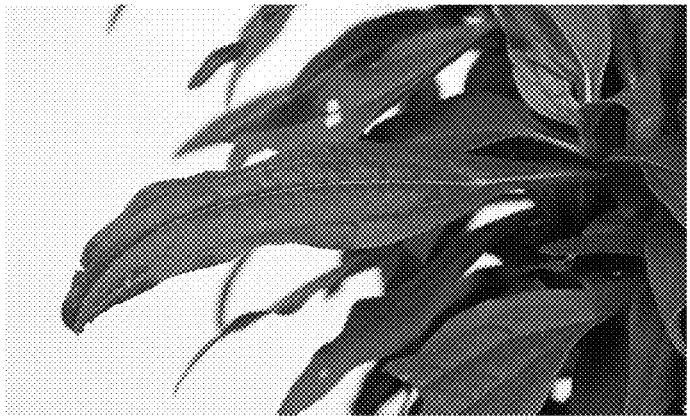

The photograph at the bottom of the second sheet (FIG. 3) is a close-up view of typical leaves of 'IFECSSCITR'.

DETAILED BOTANICAL DESCRIPTION

The aforementioned photographs and following observations and measurements describe plants grown during the summer in 17-cm containers in an outdoor nursery in Heerhugowaard, The Netherlands and under cultural practices typically used in commercial *Echinacea* production. During the production of the plants, day temperatures ranged from 16 C to 30 C and night temperatures ranged from 8 C to 18 C. Plants were 20 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSCITR'.

Parentage:

*Female parent*.—Proprietary selection of *Echinacea hybrida* identified as code number 009-17-K062-01, not patented.

*Male parent*.—Proprietary selection of *Echinacea hybrida* identified as code number 009-13-K044-04, not patented.

Propagation:

*Type*.—By in vitro meristem culture.

*Time to initiate roots, summer*.—About twelve days at temperatures about 20 C.

*Time to initiate roots, winter*.—About 16 days at temperatures about 20 C.

*Time to produce a rooted young plant, summer*.—About 36 days at temperatures about 18 C.

*Time to produce a rooted young plant, winter*.—About 42 days at temperatures about 18 C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; relatively compact and upright plant habit; broadly oblong to obovate in overall shape; freely basal branching habit with about ten primary lateral branches and about 15 secondary lateral branches developing per plant; moderately vigorous growth habit and moderate growth rate.

*Plant height*.—About 39.4 cm.

*Plant diameter or spread*.—About 36.3 cm.

*Lateral branches*.—Length: About 20.4 cm. Diameter: About 7 mm. Internode length: About 2.1 cm. Aspect: Erect to about 20 degrees from vertical. Strength: Strong. Texture: Sparsely to moderately pubescent; strigose. Color: Close to N144A and N144B; blotches, close to 137B.

Leaf description:

*Basal and cauline leaves*.—Arrangement: Alternate, simple. Length: About 10.8 cm. Width: About 3.2 cm. Shape: Lanceolate to narrowly ovate. Apex: Narrowly acute. Base: Attenuate. Margin: Mostly entire; occasionally with one or two small indentations; moderately undulate. Texture and luster, upper and lower surfaces: Sparsely pubescent, strigose and rough; matte. Venation pattern: Pinnate. Color: Developing leaves, upper surface: Close to 137C. Developing leaves, lower surface: Close to 138A. Fully expanded leaves, upper surface: Close to NN137A; venation, close to 145A. Fully expanded leaves, lower surface: Close to NN137C; venation, close to 145A.

*Petioles, basal and cauline leaves*.—Length: About 2.5 cm. Diameter: About 3 mm by 6 mm. Texture, upper and lower surfaces: Smooth, glabrous. Color, upper surface: Close to NN137A; midvein, close to 145A. Color, lower surface: Close to NN137C; midvein, close to 146D.

Inflorescence description:

*Appearance*.—Single-type inflorescences with ray and disc florets arranged on a capitulum; inflorescences positioned upright above the foliar plane on mostly upright and strong peduncles.

*Flowering habit*.—Freely flowering habit with about 26 developing and fully developed inflorescences per plant.

*Fragrance*.—Moderately fragrant; sweet and pleasant.

*Time to flower*.—Plants flower continuously from late June into late September in The Netherlands.

*Inflorescence longevity*.—Inflorescences maintain good substance for about three weeks on the plant; inflorescences persistent.

*Inflorescence buds*.—Height: About 2.6 cm. Diameter: About 3.1 cm. Shape: Flattened globular. Color: Immature involucral bracts, close to 146A; immature ray florets, close to 150C with apices, close to 150A.

*Inflorescence size*.—Diameter: About 9.8 cm. Depth (height): About 4 cm. Disc diameter: About 3.9 cm.

*Receptacles*.—Height: About 1.1 cm. Diameter: About 1.3 cm. Shape: Broadly ovate. Color: Close to 155D.

*Ray florets*.—Quantity and arrangement: About 22 to 25 arranged in a single whorl at the base of the receptacle. Length: About 4.8 cm. Width: About 1.6 cm. Shape: Narrowly oblong to oblanceolate; slightly carinate. Apex: Praemorse. Base: Cuneate. Margin: Entire. Texture and luster, upper surface: Smooth, glabrous; matte. Texture and luster, lower surface: Smooth, glabrous; slightly glossy. Aspect: About -5 degrees from horizontal; with development, apices curled slightly downward. Color: When opening, upper surface: Close to a blend of 13A and 17C. When opening, lower surface: Close to 16C. Fully opened, upper surface: Slightly darker than 14A; venation, slightly darker than 14A; color becoming closer to 17C and distally, slightly tinged with close to 151B, with subsequent development. Fully opened, lower surface: Close to 16C; venation, close to 16C; color becoming closer to 15D slightly tinged with close to 144B to 144C with subsequent development.

*Disc florets*.—Quantity and arrangement: About 500 per inflorescence, arranged spirally at the center of the inflorescence. Length: About 1 cm. Diameter: About 3 mm. Shape: Tubular; proximal 15% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 151A. Mid-section and base: Close to 145A. Color, fully opened, inner and outer surfaces: Apex: Close to 151B. Mid-section: Close to 144A. Base: Close to 151D.

*Receptacle spines*.—Quantity: One per disc floret; about 500 per inflorescence. Shape: Acicular. Apex: Acute. Base: Attenuate. Texture and luster: Smooth, glabrous; glossy. Color: Apex: Close to 14B. Mid-section: Close to 143C. Base: Close to 157D.

*Involucral bracts*.—Quantity per inflorescence: About 110 arranged in about four whorls. Length: About 1.2 cm. Width: About 3.5 mm. Shape: Narrowly ovate; strongly reflexed. Apex: Acute. Base: Cuneate. Margin: Entire. Texture and luster, upper surface: Smooth, glabrous; moderately glossy. Texture and luster, lower surface: Moderately pubescent; margins, moderately pubescent; matte. Color, upper surface: Close to 137B. Color, lower surface: Close to 137C.

*Peduncles*.—Length: About 12 cm. Diameter: About 5 cm. Strength: Strong. Aspect: Mostly upright. Texture: Sparsely pubescent; strigose. Color: Close to N144A and N144B with blotches, close to 143A and 143B.

*Reproductive organs*.—Androecium (present on ray and disc florets): Quantity per floret: Five. Filament length: About 4 mm. Filament color: Close to 160D. Anther length: About 4 mm. Anther shape: Linear. Anther color: Close to 200A to slightly darker than 200A. Pollen amount: Moderate. Pollen color: Close to 17A. Gynoecium (present only on disc florets): Quantity per floret: One. Pistil length: About 9 mm. Stigma shape: Decurrent, unequal. Stigma color: Close to 151A. Style length: About 6.5 mm. Style color: Slightly lighter than 146D. Ovary color: Close to 157C. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35 C and to be hardy to USDA Hardiness Zones 3 to 4.

It is claimed:

1. A new and distinct *Echinacea* plant named 'IFECSS-CITR' as illustrated and described.

* * * * *